United States Patent [19]

Gryaznov et al.

[11] Patent Number: 5,684,143

[45] Date of Patent: Nov. 4, 1997

[54] OLIGO-2'-FLUORONUCLEOTIDE N3'->P5' PHOSPHORAMIDATES

[75] Inventors: Sergei Gryaznov, San Mateo; Ronald G. Schultz, Fremont, both of Calif.

[73] Assignee: Lynx Therapeutics, Inc., Hayward, Calif.

[21] Appl. No.: 603,566

[22] Filed: Feb. 21, 1996

[51] Int. Cl.$^6$ .................. C07H 21/00; C07H 21/02; C07H 21/04

[52] U.S. Cl. .................. 536/23.1; 536/24.3; 536/24.5; 536/25.1

[58] Field of Search .................. 514/44; 536/23.1, 536/24.5, 25.1, 24.3; 435/6, 91.1, 172.1

[56] References Cited

U.S. PATENT DOCUMENTS 5,476,925  12/1995  Lestinger et al. .................. 536/23.1

FOREIGN PATENT DOCUMENTS

| | | |
|---|---|---|
| 2077314 | 3/1993 | Canada. |
| 0490281 A1 | 6/1992 | European Pat. Off.. |
| 0552766 A2 | 7/1993 | European Pat. Off.. |
| 4129318 A1 | 9/1991 | Germany. |

OTHER PUBLICATIONS

Abraham, et al., "A Phosphoramidite–Based Synthesis of Phosphoramidate Amino Acid Diesters of Antiviral Nucleosides," *Nucleosides & Nucleotides* 13:1891–1903 (1994).

Agrawal, et al., "Oligodeoxynucleoside Phosphoramidates and Phosphoro–thioates as Inhibitors of Human Immunodeficiency Virus," *Proc. Natl. Acad. Sci. USA* 85:7079–7083 (1988).

Azhayev, et al., "Synthesis of Phosphoramidate Analogs of Ribonucleo–side Phosphates," *Coll. Czechoslov. Chem. Commun.* 44:792–798 (1979).

Azhayev, et al., "Aminonucleosides and Their Derivatives. IX. Synthesis of Short Oligoribonucleotide with Phosphoramide Internucleotide Bonds," *Bioorganicheskaya Khimiya* 8:1218–1224 (1982). [translation attached].

Azhayev, et al., "Synthesis of Phosphoramidate Analogues of Short Oligoribunucleotides," *Nuc. Acids Res., Synm. Series No.* 9, pp. 251–254 (1981).

Bannwarth, "166. Solid–Phase Synthesis of Oligodeoxynucleotides Containing Phosphoramidate Internucleotide Linkages and Their Specific Chemical Cleavage," *Helvetica Chim. Acta* 71:1517–1527 (1988).

Chen, et al., "Synthesis of Oligonucleotide N3'→P5' Phosphoramidates," *Nuc. Acids Res.* 23:2661–2668 (1995).

Dagle, et al., "Physical Properties of Oligonucleotides Containing Phosphoramide–Modified Internucleoside Linkages," *Nuc. Acids Res.* 19:1805–1810 (1991).

Gryaznov, et al., "Synthesis and Properties of Oligonucleotides Containing Aminodeoxythymidine Units," *Nuc. Acids Res.* 20:3403–3409 (1992).

Gryaznov, et al., "Oligonucleotide N3'→N5' Phosphoramidates: Synthesis and Hybridization Properties," *J. Am. Chem. Soc.* 116:3143–3144 (1994).

Gryaznov, et al., "Oligonucleotide N3'→N5' Phosphoramidates," *Proc. Natl. Acad. Sci. USA* 92:5798–5802 (1995).

Herdewijn, et al., "Synthesis and Biological Activity of the Mono– and Diamino Analogues of 2'–Deoxyadenosine, Cordycepin, 9–(3–deoxyβ–D–threopentofuranosyl)–adenine," *Nucleosides & Nucleotides* 8:1231–1257 (1989).

Imazawa, et al., "Synthesis of 3'–azido–2',3'–dideoxyribofuranosyl–purines," *J. Org. Chem.* 43:3045–3047 (1978).

Krayevsky, et al., "Synthesis of Oligonucleotides with 5'→3' Phospho–amidoester Bond," *Nuc. Acids Res., Sym. Series No.* 9, pp. 203–205 (1981).

Mag, et al., "Synthesis and Selective Cleavage of Oligodeoxyribonucleosides Containing Non–Chiral Internucleotide Phosphoramide Linkages," *Nuc. Acids Res.* 17:5973–5988 (1989).

Mag, et al., "Synthesis and Selective Cleavage of an Oligodeoxynucleotide Containing a Bridged Non–Chiral Internucleotide 3'–Phosphoramidate Linkage," *Tetrahedron Lett.* 33:7319–7322 (1992).

Mag, et al., "Synthesis of Dinucleotides Containing a Bridged Non–Chiral Internucleoside 5'– or 3'–phosphoramidate Linkage," *Tetrahedron* 50: 10225–10234 (1994).

Milligan, et al., "Current Concepts in Antisense Drug Design," *J. Med. Chem.* 36:1923–1937 (1993).

Saha, et al., "Synthesis of Modified Achiral Internucleoside Linkages: NCHCH$_2$CH$_2$–Linked Oligonucleosides," *Tetrahedron Lett.* 34:6017–6020 (1993).

Uhlmann, et al., "Antisense Oligonucleotides: a New Therapeutic Principal," *Chem. Rev.* 90:543–584 (1990).

Williams, et al., "Properties of 2'–fluorothymidine–Containing Oligonucleotides: Interaction with Restriction Endonuclease EcoRV," *Biochem.* 30:4001–4009 (1991).

Zaitseva, et al., "Aminonucleosides and Their Derivatives. X. 2'–deoxydinucleoside Phosphates and Deoxydinucleotides with Phosphoamide Bonds," *Bioorganicheskaya Khimiya* 10:401–407 (1984). [translation attached].

Zielinski, et al., "Oligomerization of Activated Derivatives of 3'–amino–3'–deoxyguanosine on poly(C) and poly(G) Templates," *Nuc. Acids Res.* 13:2469–2484 (1985).

Zielinski, et al., "Autocatalytic Synthesis of a Tetranucleotide Analog," *Nature* 327:346–347 (1987).

(List continued on next page.)

*Primary Examiner*—George C. Elliott
*Assistant Examiner*—Sean McGarry
*Attorney, Agent, or Firm*—Stephen C. Macevicz; Vincent M. Powers

[57] ABSTRACT

A new class of oligonucleotide N3'→P5' phosphoramidates having 2' fluoro substituents are provided that have superior acid stability. The invention includes oligo-2'-fluoronucleotide N3'→P5' phosphoramidates, methods of synthesis, and duplexes and triplexes formed with DNA and RNA. Compounds of the invention are useful where the formation of stable and specific duplex and/or triplex structures is desired, including antisense and/or anti-gene pharmaceuticals, branched DNA components, DNA and/or RNA capture agents, components of DNA-based diagnostic assays, and the like.

16 Claims, 5 Drawing Sheets

OTHER PUBLICATIONS

Zielinski, et al., "Oligoaminonucleotiside Phosphoramidates, Oligomerization of Dimers of 3'-amino-3'-deoxy-nucleotides (GC and CG) in Aqueous Solution," *Nuc. Acids Res.* 15:1699:1715 (1987).

Kawasaki, A. et al "Uniformly Modified 2'-Deoxy-fluoro Phosphorothioate Oligonucleotides as Nuclease-Resistant Antisense Compounds with High Affinity and Specifcity for RNA Targets." *J. Med. Chem* 1993 vol. 36 pp. 831–841.

Pieken, W. et al "Kinetic Characterization of Ribonuclease Resistant 2'-Modified Hammerhead Ribozymes." *Science* vol. 253 pp. 314–317, 1991.

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 10 nucleotides
        ( B ) TYPE: nucleic acid
        ( C ) STRANDEDNESS: single ( D ) TOPOLOGY: linear ( x i ) SEQUENCE DESCRIPTION: SEQ ID NO: 1:

UUUUUUUUT     10

( 2 ) INFORMATION FOR SEQ ID NO: 2:

( i ) SEQUENCE CHARACTERISTICS:
        ( A ) LENGTH: 11 nucleotides
        ( B ) TYPE: nucleic acid
        ( C ) STRANDEDNESS: single
        ( D ) TOPOLOGY: linear     ( x i ) SEQUENCE DESCRIPTION: SEQ ID NO: 2:

CUUCUUCCUU A     11

( 2 ) INFORMATION FOR SEQ ID NO: 3:

( i ) SEQUENCE CHARACTERISTICS:
        ( A ) LENGTH: 13 nucleotides
        ( B ) TYPE: nucleic acid
        ( C ) STRANDEDNESS: single
        ( D ) TOPOLOGY: linear     ( x i ) SEQUENCE DESCRIPTION: SEQ ID NO: 3:

ATAAGGAAGA AGC     13

( 2 ) INFORMATION FOR SEQ ID NO: 4:

( i ) SEQUENCE CHARACTERISTICS:
        ( A ) LENGTH: 13 nucleotides
        ( B ) TYPE: nucleic acid
        ( C ) STRANDEDNESS: single
        ( D ) TOPOLOGY: linear     ( x i ) SEQUENCE DESCRIPTION: SEQ ID NO: 4:

AUAAGGAAGA AGC     13

OLIGO-2'-FLUORONUCLEOTIDE N3'->P5' PHOSPHORAMIDATES

The invention relates generally to nucleic acid polymer chemistry, and more particularly, to oligo-2'-fluoronucleotide N3'→P5' phosphoramidates, methods of synthesizing such compounds, and uses thereof.

BACKGROUND

Nucleic acid polymer chemistry has played a crucial role in many developing technologies, particularly in the pharmaceutical, diagnostic, and analytical fields, and more particularly in the subfields of antisense and anti-gene therapeutics, combinatorial chemistry, branched DNA signal amplification, and array-based DNA diagnostics and analysis e.g. Uhlmann and Peyman, Chemical Reviews, 90:543–584 (1990); Milligan et at, J. Med. Chem. 36:1923–1937 (1993); Mesmaeker et at, Current Opinion in Structural Biology, 5: 343–355 (1995); Thuong et at, Angew. Chem. Int. Ed. Engl., 32:666–690 (1993); Brenner et at, Proc. Natl. Acad. Sci., 89:5381–5383 (1992); Gold et at, Ann. Rev. Biochem., 64: 763–797 (1995); Gallop et at, J. Med. Chem. 37:1233–1258 (1994); Gordon et al, J. Med. Chem. 37: 1385–1401 (1994); Gryaznov, International application PCTFUS94/07557; Urdea et at, U.S. Pat. No. 5,124,246; Southern et at, Genomics, 13:1008–1017 (1992); McGall et at, U.S. Pat. No. 5,412,087; Fodor et at, U.S. Pat. No. 5,424,186; Pirrung et at, U.S. Pat. No. 5,405,783; and the like.

Much of this chemistry has been directed to improving the binding strength, specificity, and nuclease resistance of natural nucleic acid polymers, such as DNA. Unfortunately, improvements in one property, such as nuclease resistance, often involve trade-offs against other properties, such as binding strength. Examples of such trade-offs abound: peptide nucleic acids (PNAs) display good nuclease resistance and binding strength, but have reduced cellular uptake in test cultures, e.g. Hanvey et at, Science, 258: 1481–1485 (1992); phorphorothioates display good nuclease resistance and solubility, but are typically synthesized as P-chiral mixtures and display several sequence-non-specific biological effects, e.g. Stein et at, Science, 261:1004–1012 (1993); methylphosphonates display good nuclease resistance and cellular uptake, but are also typically synthesized as P-chiral mixtures and have reduce duplex stability, e.g. Mesmaeker et al (cited above); and so on.

Recently, a new class of oligonucleotide analog has been developed having so-called N3'→P5' phorphoramidate internucleoside linkages. These compounds display very favorable binding properties, nuclease resistance, and solubility, but like most other phosphoramidates have reduced stability under acidic conditions, Gryaznov and Letsinger, Nucleic Acids Research, 20:3403–3409 (1992); Chen et at, Nucleic Acids Research, 23: 2661–2668 (1995); Gryaznov et at, Proc. Natl. Acad. Sci., 92:5798–5802 (1995); and Gryaznov et al, J. Am. Chem. Soc., 116:3143–3144 (1994).

The utility of this new class of oligonucleotide analog would be significantly increased if modifications could be found that broadened its range of acid stability, without a concomitant loss in any other of its other favorable properties outlined above.

SUMMARY OF THE INVENTION

In view of the above, an important objective of our invention is to provide oligonucleotide N3'→P5' phosphoramidate compounds that have increased acid stability and at the same time retain favorable binding and nuclease resistance properties.

Another objective of our invention is to provide a class of compounds that are capable of forming Watson-Crick duplexes of greater stability and of comparable specificity to that of natural DNAs and RNAs.

Yet another objective of our invention is to provide a class of compounds that are capable of forming triplex structures with Watson-Crick duplexes of DNA and other nucleic acid polymers.

A further objective of our invention is to provide compounds that can be advantageously used in techniques requiting the formation of stable and specific duplex and/or triplex structures, including antisense and/or anti-gene pharmaceuticals, branched DNA components, DNA and/or RNA capture agents, and components of DNA-based diagnostic assays.

These and other objects of our invention are accomplished with oligo-2'-fluoronucleoside N3'→P5' phosphoramidates. Preferably, oligo-2'-fluoronucleoside N3'→P5' phosphoramidates of the invention have the following formula:

wherein B is a purine or pyrimidine, $R^1$ is hydroxyl or a 5'-hydroxyl protecting group, $R^2$ is hydroxyl or amino, $R^3$ is hydrogen or fluorine, $R^4$ is hydrogen or a phosphate protecting group, and n is an integer greater than 1.

Preferably, oligo-2'-fluoronucleoside N3'→P5' phosphoramidates of the invention are synthesized on solid phase supports using monomers of the invention. In further preference, synthesis takes place by nucleotide-by-nucleotide addition to a growing oligo-2'-fluoronucleotide N3'→P5' phosphoramidate chain such that the order and identity of the nucleotide monomer added at each step is controlled. That is, the sequence of B's and the length of the oligomer synthesized is predetermined.

Definitions

Whenever an oligonucleotide is represented by a sequence of letters, such as "ATGUCCTG," it will be understood that the nucleotides are in 5'→3' order from left to right and that "A" denotes deoxyadenosine, "C" denotes deoxycytidine, "G" denotes deoxyguanosine, "T" denotes thymidine, and "U" denotes deoxyuridine, unless otherwise noted.

As used herein, "N3'→P5' phosphoramidate" refers to an internucleosidic linkage of the form:

3'—NH—P(=O)(OR⁴)—O— 5' wherein the 3' and 5' refer to the carbon atoms of the sugar moieties of consecutive nucleosides which are connected by way of the linkage, and wherein $R^4$ is hydrogen or a phosphate protecting group. More particularly, $R^4$ may by alkyl, alkenyl, aryl, aralkyl, or cycloalkyl containing up to 10 carbon atoms. Preferably, $R^4$ is alkyl having from 1 to 6 carbon atoms; electron- withdrawing β-substituted ethyl, particularly β-trihalomethyl-, β-cyano-, β-sulfo-, β-nitro-substituted ethyl, or the like; electron-withdrawing substituted phenyl, particularly halo-, sulfo-, cyano-, or nitro-, substituted phenyl; or electron-withdrawing substituted phenylethyl. More preferably, $R^4$ is methyl, β-cyanoethyl, or 4-nitrophenylethyl. Most preferably, $R^4$ is hydrogen, methyl, or β-cyanoethyl. Electron-withdrawing substituents are typically halo, cyano, nitro, sulfo, or mono-, di-, or trihalomethyl, and the like. Halogen atom substituents are usually fluoro, chloro, bromo, or iodo; and preferably, they are fluoro or chloro. "Electron-withdrawing" denotes the tendancy of a substituent to attract valence electrons of the molecule of which it is apart, i.e. it is electronegative, e.g. March, Advanced Organic Chemistry, pgs. 16–18 (John Wiley, New York, 1985). For convenience, nucleotide phosphoramidates are sometimes indicated herein by a subscripted "np" or "pn" for N3'→P5' phosphoramidates and P3'→N5' phosphoramidates, respectively. Thus, "$U_{np}U$" is a dinucleotide in which a 3'-aminouridine and a deoxyuridine are linked by an N3'→P5' phosphoramidate linkage. Similarly, 2'-fluoro substituents are indicated by a superscripted "f". Thus, "$U^f_{np}U$" is a dinucleotide in which the 3'-most 2'-fluorouridine is linked to a uridine by an N3'→P5' phosphoramidate linkage. A single leading subscripted "p" indicates to a 5' monophosphate, and a single trailing subscripted "n" indicates a 3'-amino.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, e.g. stability, specificity, or the like, such as disclosed by Uhlmann and Peyman (cited above).

As used herein, "pyrimidine" means the pyrimidine occurring in natural nucleosides, including cytosine, thymine, and uracil, and common analogs thereof, such as those containing oxy, methyl, methoxy, hydroxyl, amino, thio, and like, substituents. The term as used herein further includes pyrimidines with common protection groups attached, such as 4N-benzoylcytosine. Further common pyrimidine protection groups are disclosed by Beaucage and Iyer, Tetrahedron, 48:2223–23 11 (1992).

As used herein, "purine" means the purines occurring in natural nucleosides, including adenine, guanine, and hypoxanthine, and common analogs thereof, such as those containing oxy, methyl, methoxy, hydroxyl, amino, thio, and like, substituents. The term as used herein further includes purines with common protection groups attached, such as 2N-benzoylguanine, 2N-isobutrylguanine, 6N-benzoyladenine, and the like. Further common purine protection groups are disclosed by Beaucage and Iyer (cited above).

DETAILED DESCRIPTION OF THE INVENTION

The invention includes polymers of 2'-fluoro-3'-aminonucleosides, that is, oligo-2'-fluoronucleotide N3'→P5' phosphoramidates, monomers and methods for solid phase assembly of such polymers, and uses of the polymers. The invention also includes compositions comprising Watson-Crick duplexes of RNA or DNA and oligo-2'-fluoronucleotide N3'→P5' phosphoramidates and compositions comprising triplexes of DNA duplexes and oligo-2'-fluoronucleotide N3'→P5' phosphoramidates, and methods and kits for using oligo-2'-fluoronucleotide N3'→P5' phosphoramidates as DNA capture agents based on either Watson-Crick basepairing with single stranded target nucleic acids or Hoogsteen or reverse Hoogsteen triplet formation with double stranded target nucleic acids.

Preferably, oligo-2'-fluoronucleotide N3'→P5' phosphoramidates of the invention are between 2 and 30 nucleotides in length. More preferably, they are between 8 and 25 nucleotides in length; and most preferably, they are between 8 and 20 nucleotides in length.

Oligomers of the invention may be synthesized by several different approaches. In a first approach, coupling is achieved by carbon tetrachloride-driven oxidative phosphorylation of a nucleoside 3'-amine by a 5'-H-phosphonate of the terminal nucleotide of a growing chain anchored to a solid phase support, as described, for example, by Gryaznov et al, J. Am. Chem. Soc. 116:3143–3144 (1994); and Chen et al, Nucleic Acids Research, 23: 2661–2668 (1995); which references are incorporated by reference. Monomers for this synthetic approach have the following form:

where B is defined as above and $R^1$ is hydrogen or a hydroxyl protecting group, such as triphenylmethyl (i.e., trityl), p-anisyldiphenylmethyl (i.e., monomethoxytrityl or MMT), di-p-anisylphenylmethyl (i.e., dimethoxytrityl or DMT), pivaloyl, acetyl, 4-methoxytetrahydropyran-4-yl, tetrahydropyranyl, phenoxyacetyl, isobutyloxycarbonyl, pixyl, benzyl, trialkylsilyl having from 3 to 9 carbon atoms, 9-fluorenylmethyl carbamate (Fmoc), or the like. Preferably, $R^1$ is DMT. Greene and Wuts, Protective Groups in Organic Synthesis, 2nd Edition (John Wiley, New York, 1991) provides extensive guidance on the selection of protecting groups for the various embodiments of the invention.

Figure 1:
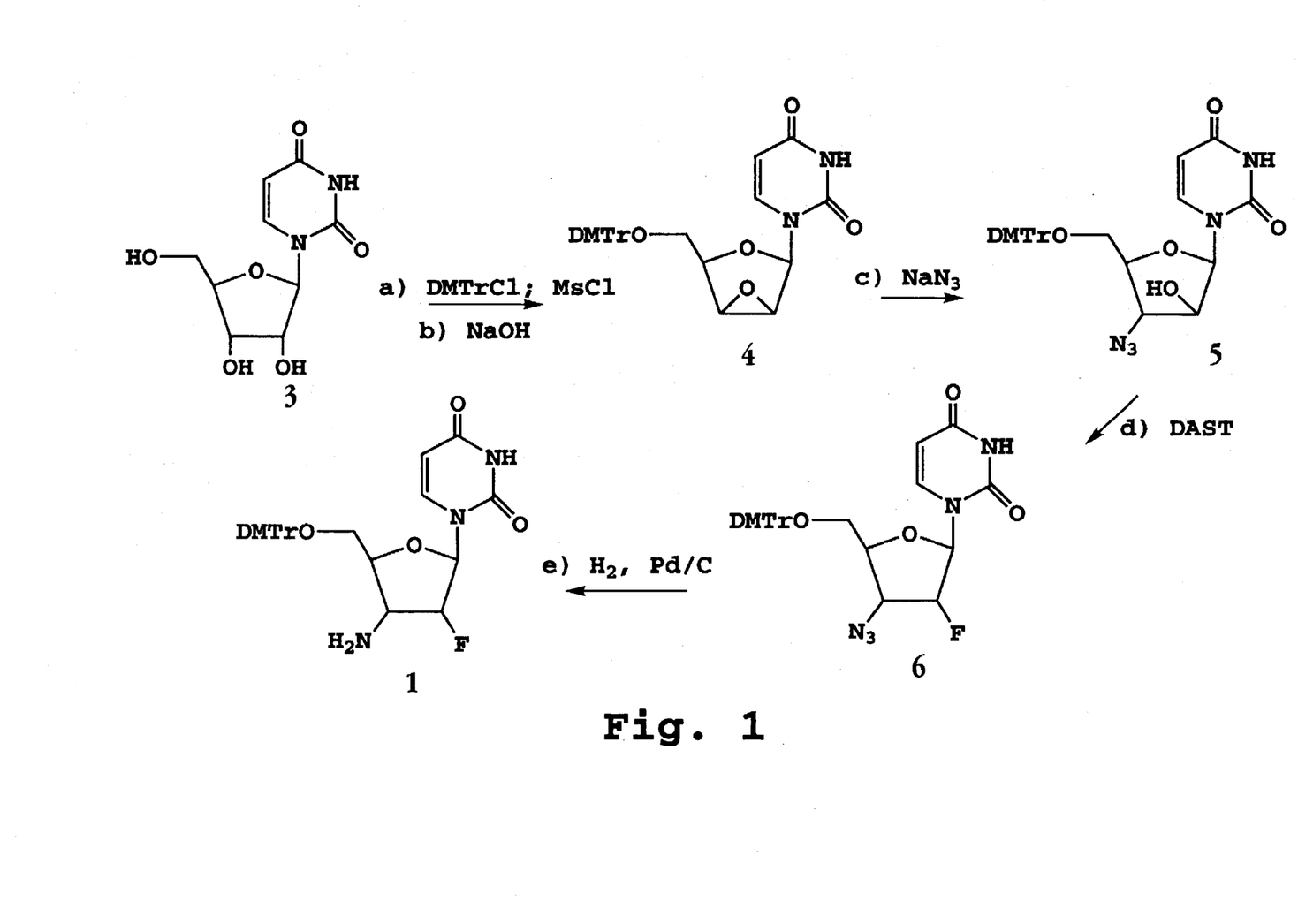
FIG. 1 illustrates a scheme for synthesizing a first type uracil monomer for assembling oligo-2'-fluoronucleoside N3'→P5' phosphoramidates of the invention.

A general scheme for preparing the above monomers is shown in FIG. 1. Briefly, a ribonucleoside is transformed into a 5'-hydroxyl-protected-2',3'-anhydroxylnucleoside, after which the 2',3'-epoxy ring is opened by treatment with sodium azide, or like reagent, to form a 5'-hydroxyl-protected-3'-azido-3'-deoxyarabinonucleoside. After purification, the 5'-hydroxyl-protected-3'-azido-3'-deoxyarabinonucleoside is fluorinated at the 2' position by treatment with diethylaminosulfur trifluoride (DAST), or like reagent, after which the azido group is reduced to give the above monomer. The monomers are then employed for chain assembly essentially as described by Chen et al and Gryaznov et al (cited above).

Figure 4:
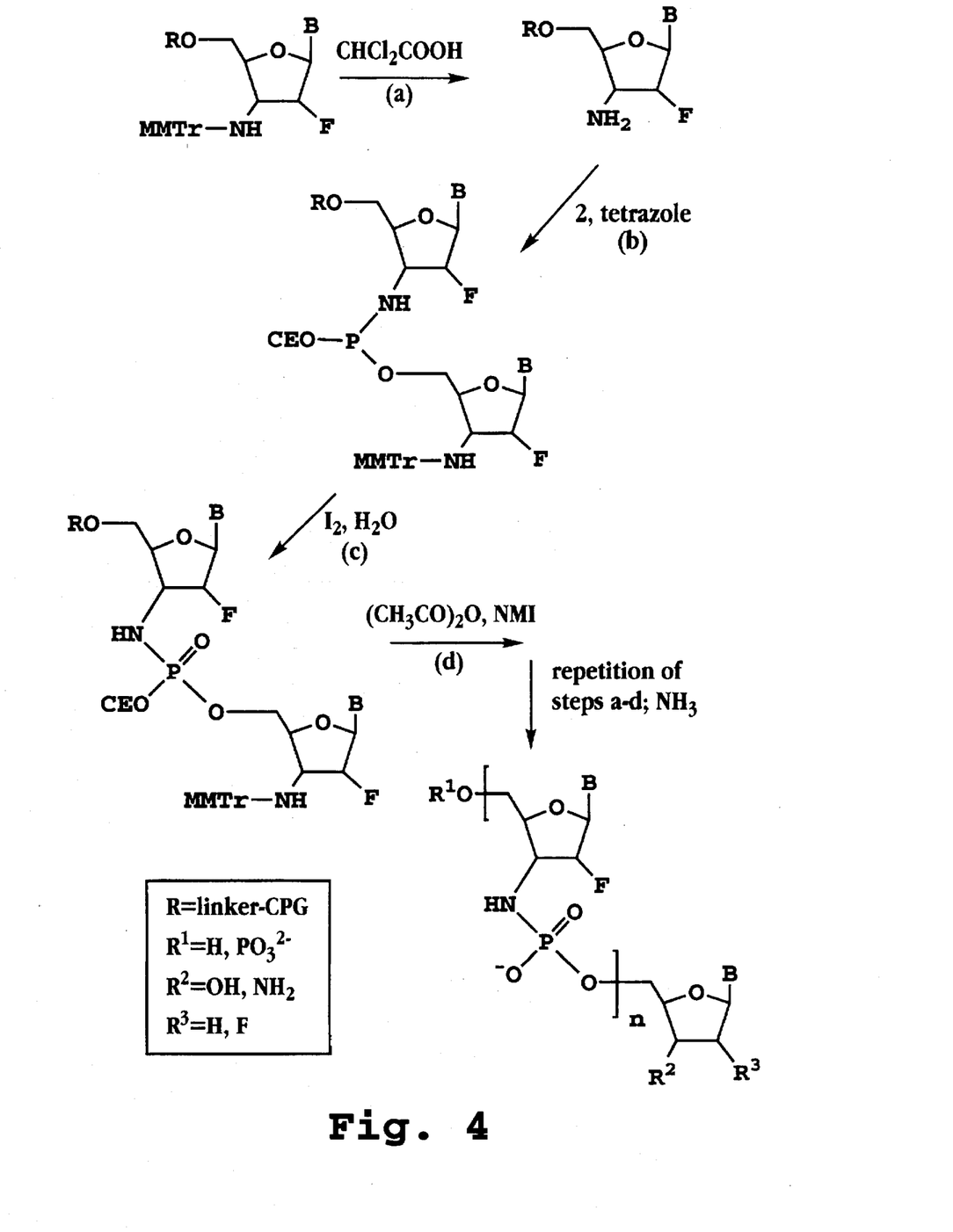
FIG. 4 illustrates a scheme for synthesizing oligo-2'-fluoronucleoside N3'→P5' phosphoramidates of the invention.

In a second approach, oligomers of the invention are synthesized via an exchange reaction between a phosphoramidite group on a monomer and a 3'-amino of an anchored chain, as illustrated by Scheme 4 in FIG. 4. Monomers for this synthetic approach have the following form:

where B and $R^1$ are defined as above, $R^5$ is an amino protecting group, and R' and R" taken together with the nitrogen form an alkyl- or arylamino leaving group. More particularly, R' and R" taken separately each are alkyl, aralkyl, cycloalkyl, and cycloalkylalkyl containing up to 10 carbon atoms in total. Preferably R' and R" taken separately are alkyl having from 1 to 5 carbon atoms. Most preferably, R' and R" taken separately are isopropyl. R' and R" taken together form an alkylene chain containing up to 5 carbon atoms in the principal chain and a total of up to 10 carbon atoms with both terminal valence bonds of said chain being attached to the nitrogen atom to which R' and R" are attached; or R' and R" when taken together with the nitrogen atom to which they are attached form a saturated nitrogen heterocycle which may contain one or more additional heteroatoms from the group consisting of nitrogen, oxygen, and sulfur. More preferably, R' and R" taken together and with the nitrogen to which they are attached are pyrrolidino, morpholino, or piperidino. Most preferably, R' and R" taken together and with the nitrogen to which they are attached are morpholino. Preferably, $R^5$ is trityl, and more preferably, $R^5$ is 4-methoxytrityl.

Figure 2:
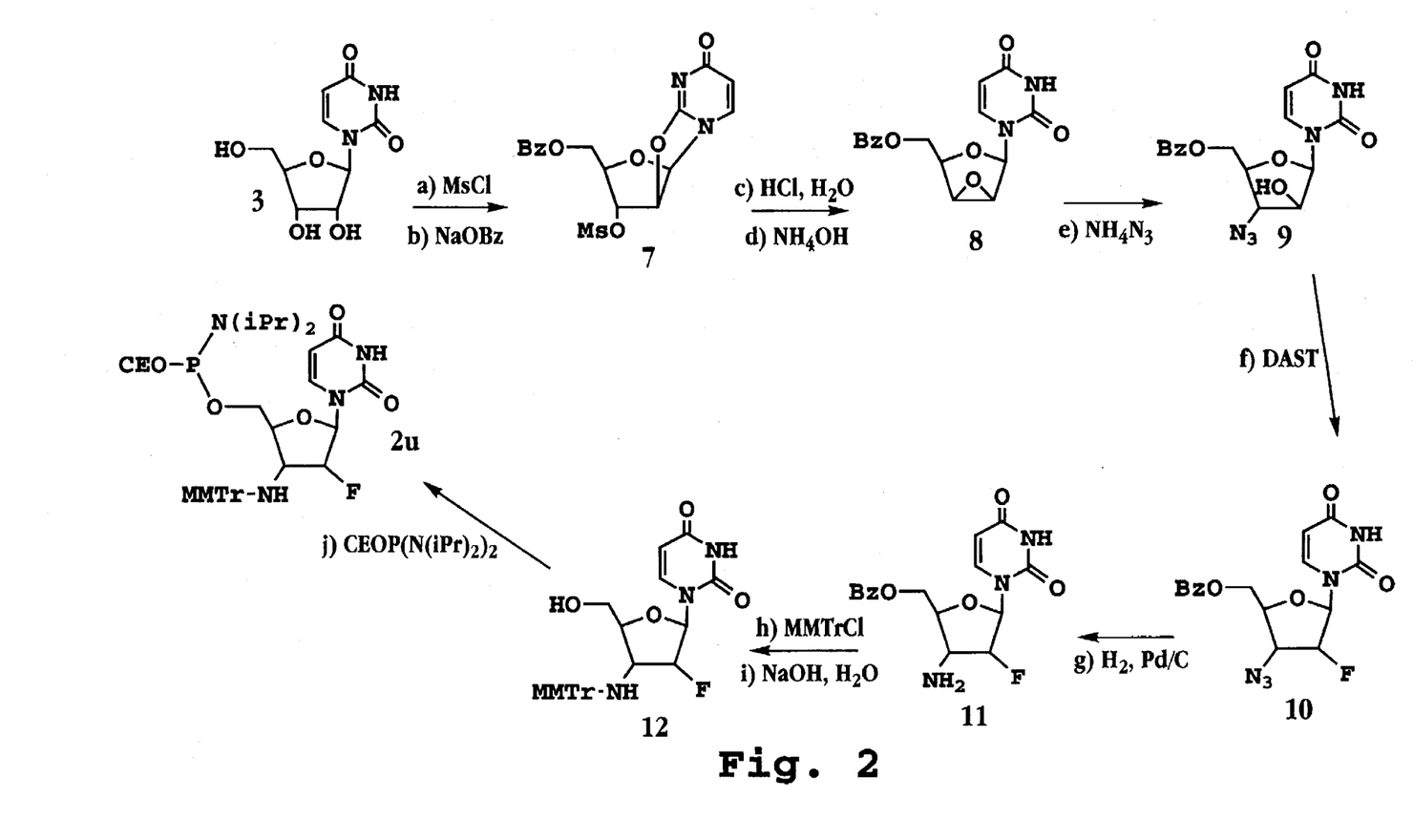
FIG. 2 illustrates a scheme for synthesizing a second type uracil monomer for assembling oligo-2'-fluoronucleoside N3'→P5' phosphoramidates of the invention.
Figure 3:
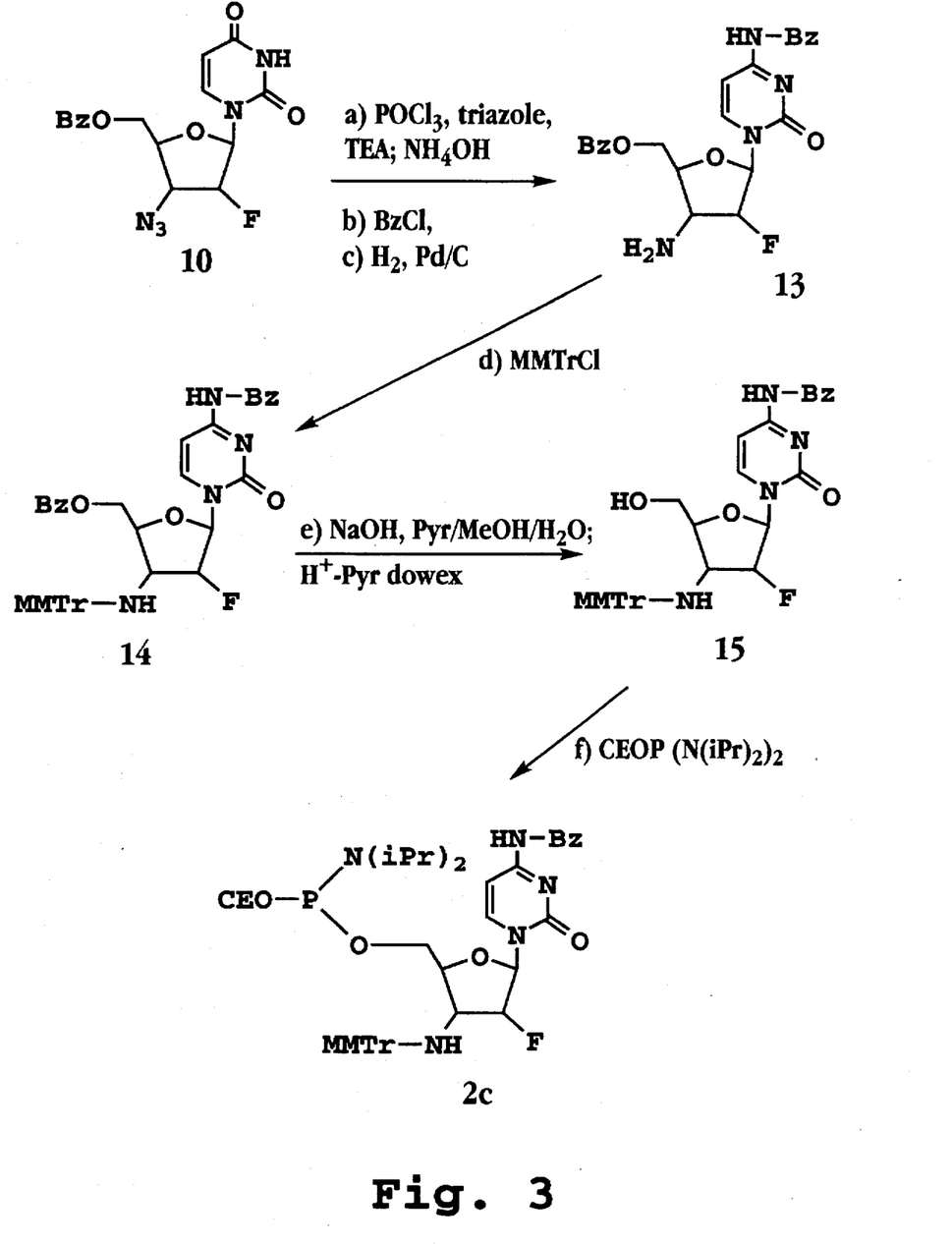
FIG. 3 illustrates a scheme for synthesizing cytosine monomers for assembling oligo-2'-fluoronucleoside N3'→P5' phosphoramidates of the invention.

Phosphoramidite monomers of the invention are prepared as follows, as illustrated in FIGS. 2 and 3. As above, a ribonucleoside is transformed into a 5'-hydroxyl-protected-2',3'-anhydroxylnucleoside, after which the 2',3'-epoxy ring is opened by treatment with sodium azide, or like reagent, to form a 5'-hydroxyl-protected-3'-azido-3'-deoxyarabinonucleoside. After purification, the 5'-hydroxyl-protected-3'-azido-3'-deoxyarabinonucleoside is fluorinated at the 2' position by treatment with diethylaminosulfur trifluoride (DAST), or like reagent, after which the azido group is reduced to give a 3'-amino. After suitably protecting the 3'-amino and releasing the 5'-hydroxyl protecting group, the nucleoside is phosphitylated at the 5' oxygen to give the crude phorphoramidite monomer.

The phosphoramidite monomers are used in the following synthetic cycle:

1) detritylation with acid of the 3'-amino group of nucleoside attached to a solid support through 5'-terminus;

2) tetrazole-catalyzed amidite transfer reaction between the phosphoramidite monomer and the 3'-amino group of the nucleoside on a solid support, resulting in formation of an internucleoside phosphoramidite diester group; this may be repeated with intermediate washing with acetonitrile, or like solvent, to achieve slightly higher efficiency of chain elongation;

3) oxidation of the newly formed internucleoside phosphoramidite diester into a phosphoramidate diester group with aqueous iodine, or like oxidizing agent;

4) capping of unreacted 3'-amino groups with acetic anhydride, or like capping agent.

This cycle can be repeated, resulting in oligo-2'-fluoronucleotide N3'→P5' phosphoramidates after cleavage from the solid support and deprotection with ammonia.

A wide variety of solid phase supports may be used with the invention, including microparticles made of controlled pore glass (CPG), highly cross-linked polystyrene, acrylic copolymers, cellulose, nylon, dextran, latex, polyacrolein, and the like, disclosed in the following exemplary references: Meth. Enzymol., Section A, pages 11–147, vol. 44 (Academic Press, New York, 1976); U.S. Pat. Nos. 4,678, 814; 4,413,070; and 4,046;720; and Pon, Chapter 19, in Agrawal, editor, Methods in Molecular Biology, Vol. 20, (Humana Press, Totowa, N.J., 1993). Supports further include commercially available nucleoside-derivatized CPG and polystyrene beads (e.g. available from Applied Biosystems, Foster City, Calif.); polystyrene grafted with polyethylene glycol (e.g., TentaGel™, Rapp Polymere, Tubingen Germany); and the like. Selection of the support characteristics, such as material, porosity, size, shape, and the like, and the type of linking moiety employed depends on a variety of factors, such as protection groups employed, length of final product, quantity of final product, and the like. Exemplary linking moieties are disclosed in Pon et at, Biotechniques, 6:768–775 (1988); Webb, U.S. Pat. No. 4,659,774; Barany et al, International patent application PCTFLIS91/06103; Brown et al, J. Chem. Soc. Commun., 1989: 891–893; Damha et at, Nucleic Acids Research, 18:3813–3821 (1990); Beattie et al, Clinical Chemistry, 39:719–722 (1993); Maskos and Southern, Nucleic Acids Research, 20: 1679–1684 (1992); and the like.

Preferably, thermal stability of oligo-2'-fluoronucleotide N3'→P5' phosphoramidates are determined by way of melting, or strand dissociation, curves. The temperature of fifty percent strand dissociation is taken as the melting temperature, $T_m$, which, in turn, provides a convenient measure of stability. $T_m$ measurements are typically carried out in a saline solution at neutral pH with target and oligomer concentrations at between about 1.0–3.0 μM. Typical conditions are as follows: 150 mM NaCl and 10 mM $MgCl_2$ in a 10 mM sodium phosphate buffer (pH 7.0) or in a 10 mM Tris-HCl buffer (pH 7.0); or like conditions. Data for melting curves are accumulated by heating a sample, e.g. a duplex or triplex, of the oligo-2'-fluoronucleotide N3'→P5' phosphoramidate and its complementary single stranded or double stranded oligonucleotide from 10–15° C. to about 85°–90° C. As the temperature of the sample increases, absorbance of 260 nm light is monitored at 1° C. intervals, e.g. using a Cary (Australia) model 1E or a Hewlett-Packard (Palo Alto, Calif.) model HP 8459 UVNIS spectrophotometer and model HP 89100A temperature controller, or like instruments.

In embodiments where triplex formation is desired, there are constraints on the selection of complementary sequences. Generally, third strand association via Hoogsteen type of binding is most stable along homopyrimidine-homopufine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al, Proc. Natl. Acad. Sci., 88:9397–9401 (1991); Roberts et at, Science, 258:1463–1466 (1992); Distefano et al, Proc. Natl. Acad. Sci., 90:1179–1183 (1993); Mergny et at, Biochemistry, 30:9791–9798 (1991); Cheng et at, L Am. Chem. Soc., 114:4465–4474 (1992); Beat and Dervan, Nucleic Acids Research, 20:2773–2776 (1992); Beat and Dervan, J. Am. Chem. Soc., 114:4976–4982 (1992); Giovannangeli et at, Proc. Natl. Acad. Sci., 89:8631–8635 (1992); Moser and Dervan, Science, 238:645–650 (1987); McShan et at, J. Biol. Chem., 267:5712–5721 (1992); Yoon et at, Proc. Natl. Acad. Sci., 89:3840–3844 (1992); Blume et al, Nucleic Acids Research, 20:1777–1784 (1992); and the like. Generally, after one of the oligonucleotide moieties forms a Watson-Crick duplex with a pyrimidine-rich or purine-rich track in a target polynucleotide, the remaining oligonucleotide components bind to the major groove of the duplex to form a triplex structure.

Compounds of the invention can be employed as diagnostic probes to detect the presence of one or more target polynucleotides in a wide range of samples, including environmental samples, e.g. from public water supplies, samples from foodstuffs, and from other biological samples, such as blood, saliva, semen, amniotic fluid, tissue homogenates of plants or animals, or of human patients, and the like. The use of nucleic acid probes in human diagnostics, forensics, and genetic analysis has been extensively reviewed. For example, the following references describe many diagnostic applications of nucleic acid probes for which the present invention can be usefully employed: Caskey, Science 236:1223–1228 (1987); Landegren et al, Science, 242:229–237 (1988); and Arnheim et al, Ann. Rev. Biochem., 61:131–156 (1992). Moreover, there is extensive guidance in the literature concerning the selection of hybridization conditions, labeling means, and the like, which is applicable to the practice of the present invention, e.g. Wetmer, Critical Reviews in Biochemistry and Molecular Biology 26:227–259 (1991); and the like.

Oligo-2'-fluoronucleoside N3'→P5' phosphoramidates of the invention may be used in essentially any of the known solution or solid phase hybridization formats, such as those in which the analyte is bound directly to a solid phase, or sandwich hybridizations in which the analyte is bound to an oligonucleotide that is, in turn, bound to a solid phase. Oligo-2'-fluoronucleoside N3'→P5' phosphoramidates are particularly useful in conjunction with branched polymer signal amplification schemes, such as those disclosed by Urdea et al, U.S. Pat. No. 5,124,246; Wang et al, U.S. Pat. No. 4,925,785; and the like. Urdea et al and Wang et al are incorporated by reference for their description of such hybridization assays. In such embodiments, the oligo-2'-fluoronucleoside N3'→P5' phosphoramidate preferably serves as a highly stable and specific "capture" probe by binding to a target polynucleotide analyte of interest.

Kits incorporating oligo-2'-fluoronucleotide N3'→P5' phosphoramidates can take a variety of forms depending on the particular embodiment, the type of assay format employed, and the labeling scheme employed. Generally, kits of the invention comprise an oligo-2'-fluoronucleoside N3'→P5' phosphoramidate specific for a given target polynucleotide, a hybridization buffer, and a signal generation moiety. Kits of the invention may further comprise wash buffers for removing unbound label and/or oligo-2'-fluoronucleoside N3'→P5' phosphoramidate, solid phase supports such as derivatized magnetic beads, or the like; and prehybridization buffers containing blocking agents, e.g. Denhardt's solution, sonicated salmon sperm DNA, detergents such as 1% SDS, or the like, for minimizing nonspecific binding of the oligo-2'-fluoronucleoside N3'→P5' phosphoramidate or other nucleosidic binding components, such as amplifier strands. An exemplary hybridization buffer comprises the following reagents: 100–150 mM NaCl, 10 mM $MgCl_2$, and 10 mM Tris-HCl (pH 7.0).

Compounds of the invention may be used as DNA capture agents by forming highly stable triplex between a double stranded target DNA and an oligo-2'-fluoronucleotide N3'→P5' phosphoramidate of a predetermined sequence. This application is particularly useful in manipulating multiple double stranded DNAs such as DNA sequencing plasmids of PCR amplicons that contain complementary sequences for binding via triplex formation with the oligo-2'-fluoronucleotide N3'→P5' phosphoramidates, such as described ordinary oligonucleotides by Cantor et at, U.S. Pat. No. 5,482,836, which patent is incorporated by reference. Preferably, compounds of the invention are biotinylated or covalently attached to a like binding moiety, such as a hapten. After contacting with target DNAs in a sample under conditions that permit triplex formation, the target DNAs are extracted from the sample by contacting the biotin, or like binding moiety, with its receptor which preferably is attached to a solid support, such as a magnetic bead. After washing, the captured DNAs may be release under conditions that destroy the stability of the triplex structure, e.g. mild alkaline buffer, pH 8–10.

Signal generation moieties are molecular structures that directly or indirectly generate a signal, e.g. fluorescent, colorimetric, radioactive, or the like, that can be detected by conventional means. Direct signal generation means that the moiety producing a signal is covalently linked to the oligo-2'-fluoronucleoside N3'→P5' phosphoramidate, e.g. as with the covalent attachment of a fluorescent dye, enzyme, or the like. Indirect signal generation means that a particular moiety, e.g. an oligonucleotide tail conjugated to a oligo-2'-fluoronucleoside N3'→P5' phosphoramidate, is one component of a multi-component system that produces a signal. Preferably, the signal generation moieties comprises an oligonucleotide tail of about 12 to about 50 nucleotides in length. In one aspect of this preferred embodiment, a signal is generated indirectly by providing a second oligonucleotide which is complementary to the tail and which has a fluorescent dye covalently attached. Attaching fluorescent dyes to oligonucleotides is well known in the art, e.g. U.S. Pat. Nos. 4,997,828; 5,151,507; 4,855,225; 5,188,934; Eckstein, editor (cited above); and the like.

Compounds of the invention can be employed as antisense or anti-gene compounds for treating disease. The components included in such pharmaceutical compositions of the invention depend on several factors, including the nature of the disease or condition being treated, the location of disease lesions, the mode of drug delivery and/or administration contemplated, the latter of which can include in vivo administration by way of regional or systemic perfusion, topical application, intranasal administration, administration by implanted or transdermal sustained release systems, and the like, as well as ex vivo administration for use in bone marrow purging. A preferred method of administration of oligonucleotides comprises either regional or systemic perfusion. According to a method of regional perfusion, the afferent and efferent vessels supplying the extremity containing a lesion, e.g. a cancerous lesion, are isolated and connected to a low-flow perfusion pump in continuity with an oxygenator and heat exchanger. The iliac vessels may be used for perfusion of the lower extremities. The axillary vessels are cannulated high in the axilla for upper extremity lesions. A pharmaceutical composition containing an oligo-2'-fluoronucleotide N3'→P5' phosphoramidate is added to the perfusion circuit, and the perfusion is continued for an appropriate time period, e.g. an hour. Perfusion rates of from 100 to 150 ml/minute may be employed for lower extremity lesions, while half that rate should be employed for upper extremity lesions. Systemic heparinization may be used throughout the perfusion, and reversed after the perfusion is complete. This isolation perfusion technique permits administration of higher dosed of chemotherapeutic agent than would otherwise be tolerated upon infusion into the arterial or venous systemic circulation.

Generally a pharmaceutical composition of the invention facilitates the delivery of an effective amount of the active drug to a desired site in a manner consistent with patient safety and comfort. An effective amount of an oligo-2'-fluoronucleotide N3'→P5' phosphoramidate depends on several factors, including the disease or condition being treated, the method of administration, the scheduling of the administration, the condition of the patient, and the like. Typically, a parentially administered dose will be in the range of about 1 g/kg/day to about 100 mg/kg/day of patient body weight. A key factor in selecting an appropriate dose for a given condition or disease is the therapeutic result, as measure by standard criteria well known to the medical practitioner, e.g. for oncological applications see: Cancer: Principles and Practice of Oncology, 3rd Edition, edited by V. T. DeVita et al (Lippincott Company, Philadelphia, 1989).

Pharmaceutical compositions of the invention include a pharmaceutical carrier that may contain a variety of components that provide a variety of functions, including regulation of drug concentration, regulation of solubility, chemical stabilization, regulation of viscosity, absorption enhancement, regulation of pH, and the like. For example, in water soluble formulations the pharmaceutical composition preferably includes a buffer such as a phosphate buffer, or other organic acid salt, preferably at a pH of between about 7 and 8. For formulations containing weakly soluble oligonucleotides, microemulsions may be employed, for example by using a nonionic surfactant such as Tween 80 in an amount of 0.04–0.05% (w/v), to increase solubility. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences, e.g. Remington's Pharmaceutical Science, latest edition (Mack Publishing Company, Easton, Pa.).

Compounds of the invention include the pharmaceutically acceptable salts thereof, including those of alkaline earths, e.g. sodium or magnesium, ammonium or $NX_4^+$, wherein X is C 1–4 alkyl. Other pharmaceutically acceptable salts include organic carboxylic acids such as acetic, lactic, tartaric, malic, isethionic, lactobionic, and succinic acids; organic sulfonic acids such as methanesulfonic, ethanesulfonic, and benzenesulfonic; and inorganic acids such as hydrochloric, sulfuric, phosphoric, and sulfamic acids. Pharmaceutically acceptable salts of a compound having a hydroxyl group include the anion of such compound in combination with a suitable cation such as $Na^+$, $NH_4^+$, or the like.

Sustained release systems suitable for use with the pharmaceutical compositons of the invention include semipermeable polymer matrices in the form of films, microcapsules, or the like, comprising polylactides, copolymers of L-glutamic acid and gamma-ethyl-L-glutamate, poly(2-hydroxyethyl methacrylate), and like materials. Sustained release systems also include liposomally entrapped oligonucleotides, e.g. as described in Liposome Technology, Vol. II, Incorporation of Drugs, Proteins, and Genetic Material (CRC Press).

Experimental Methods

Phosphodiester oligodeoxyribonucleotides and oligoribonucleotides were prepared on an ABI 380B DNA synthesizer using standard protocol via the phosphoramidite method.[18] Oligonucleotide N3'→P5' phosphoramidates, containing 2'-deoxy- and one or two 2'-fluoronucleosides were synthesized using the oxidative phosphorylation method on a ABI 394 synthesizer as previously described.[4c] Uniformly modified oligo-2'-fluoronucleotide N3'→P5' phosphoramidates were prepared by amidite transfer reaction on an ABI 380B synthesizer using the following protocol:

1) detritylation, 5% dichloroacetic acid in dichloromethane, 1 min 2) coupling, 0.1M phosphoramidite 2 and 0.45M tetrazole in acetonitrile, 3 min 3) oxidation, 0.1M iodine in tetrahydrofuran/pyridine/water, 10/10/1, v/v/v, 1 min 4) capping, acetylation of unreacted 3'-amino groups by standard ABI capping solutions, 30 sec Chemical steps within the cycle were followed by acetonitrile washings and flushings with dry argon for 0.2–0.4 min. After cleavage from the solid support and deprotection with concentrated aqueous ammonia, 1–1.5 h, 55° C., oligonucleotides were analyzed and purified by IE HPLC. Oligonucleotides were desalted on Pharmacia NAP-5 or NAP-10 gel filtration columns immediately after purification and stored frozen or lyophilized at −18° C.

Preparation of the 5'-phosphorylated oligonucleotides was done upon sulfone-derivatized CPG,[19] and 5'-hydroxyl oligomers were synthesized upon oligonucleotide-succinyl CPG.

Oligonucleotide thermal dissociation experiments were carded out as previously described,[4b] with melting buffers as listed in Table 1.

Dionex DX300 or DX500 systems were used for IE analysis and purification of oligonucleotides. A Pharmacia MonoQ 10/10 column was used for analysis and purification of crude oligomers, eluted with a 2% per minute gradient of 1.5M NaCl in 10 mM NaOH. A Dionex NucleoPac PA100 column, eluted with a 1.5% per minute gradient of 1.5M NaCl in 10 mM NaOH was used for all other IE HPLC analysis. A Hewlett Packard Hypersil ODS, 5 g column on a Waters HPLC system was used for RP HPLC, with a 1% per minute gradient of acetonitrile in 0.1M triethylammonium acetate, pH 7.0.

NMR spectra were recorded on a Bruker DRX-400 spectrometer. Chemical shifts are reported relative to TMS, $CCl_3F$, and $H_3PO_4$, for $^1H$, $^{19}F$, and $^{31}P$ spectra, respectively.

Thin layer chromatography (TLC) was performed on Whatman polyester-backed silica gel plates with methanol/ dichloromethane eluents.

Acid hydrolysis of 0.17 $OD_{260}$ of the dimer $dU^f_{np}T$ was done in 25 gL of 64% acetic acid, 2 h at 55° C., and the reaction mixture was analyzed by RP HPLC. Approximately 83% of the dimer, retention time (Rt) 15.0 min, was hydrolyzed to mainly 5'-thymidylic acid, Rt 10.6 min, and 2'-fluor-3'-aminouridine, Rt 11.2 min, as were identified by co-injection with authentic standards. Also, ~7.5% of thymidine, Rt 12.1 min, was found in the reaction mixture.

Acid hydrolysis of the oligonucleotide phosphoramidates (Table 2), 1–30$D_{260}$ of each, was carded out at room temperature in 0.1–0.2 mL of 10% acetic acid, pH 2.2 or in sodium acetate buffers, pH 4.7 and 5.3. For enzymatic digestion, 0.2 $OD_{260}$ of oligonucleotides 19 and 22 (Table 1) were treated with 0.02 units of snake venom phosphodiesterase and 0.8 units of alkaline phosphatase, both from Sigma, in 0.2 mL of Tris-HCl buffer, pH 8.9, at room temperature. Aliquots from the reaction mixtures were taken at multiple time points and analyzed by IE HPLC.

EXAMPLE 1

5'-DMT-O-2'-fluoro-3'-aminouridine

Figure 5:
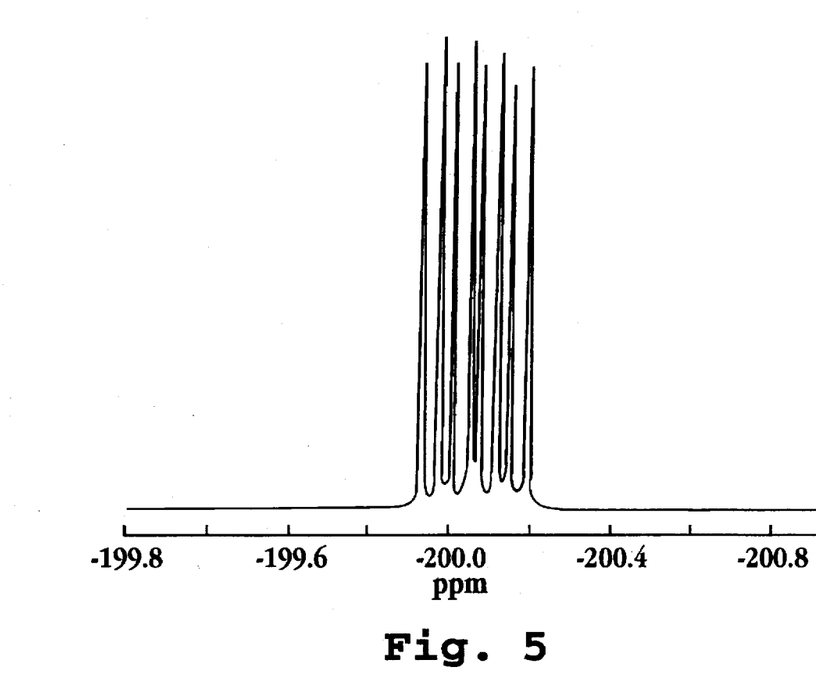
FIG. 5 is a $^{19}F$ NMR spectrum of 5'-DMT-O-2'-fluoro-3'-amino-2',3'-dideoxyuridine synthesized in accordance with the invention.

Compound 1, 5'-DMT-2'-fluoro-3'-aminouridine was prepared according to Scheme 1 shown in FIG. 1. This monomer was used for incorporation of 2'-fluoro-3'-aminouridine into oligonucleotide phosphoramidates by the oxidative phosphorylation method.[4] First, uridine 3 was transformed into the 5'-DMT-2',3'-anhydrolyxouridine 4 by successive, one pot reaction with DMT-chloride, mesyl chloride, and sodium hydroxide. The 2',3'-epoxy ring was then opened by treatment with sodium azide,[10] producing 5'-DMT-3'-azido-3'-deoxyarabinouridine 5 as the main product, and isomeric 5'-DMT-2'-azido-2'-deoxyxylouridine as a by-product, in approximately a 2:1 ratio. Compound 5 was isolated by silica gel chromatography and then fluorinated with diethylaminosulfur trifluoride (DAST) to give 6. Finally, the azido group of 6 was reduced with hydrogen over palladium catalyst, giving 5'-DMT-2'-fluoro-3'-aminouridine 1. The structure of nucleoside 1 was confirmed by $^1H$ and $^{19}F$ NMR analysis and by mass spectrometry (FIG. 5). More particularly, the steps were carded out as follows:

5'-O-DMT-2',3'-anhydrolyxouridine (compound 4, FIG. 1) was prepared as follows: To 10.0 g (41 mmol) of dry 3 in 250 mL anhydrous pyridine was added 14.6 g (43 mmol) of dimethoxytrityl chloride. The mixture was stirred overnight, then cooled on ice and 8.0 mL (103 mmol) methanesulfonyl chloride was added. After stirring at room temperature for 4 h, the reaction was quenched with 1 mL $H_2O$ and the solvent removed in vacuo. The residue was suspended in 500 mL $CH_2Cl_2$, washed with water (3×250 mL), and reconcentrated in vacuo to a foam. The foam was dissolved in 450 mL dioxane and 250 mL of 1N NaOH added. After stirring for 4 h, the dioxane was removed in vacuo, and the resultant slurry extracted with 500 mL of $CH_2Cl_2$. Concentration of the $CH_2Cl_2$ layer and flash chromatography provided 13.8 g (64%) of product as a light yellow powder. Mass-spectrometry, FAB$^+$, M+H$^+$, calculated: 529.1975, observed: 529.1963. $^1H$ NMR δ7.58 (d, J=8.2 Hz, 1H), 7.5–7.2 (mm, 10H), 6.86 (d, J=8.2 Hz, 4H), 6.20 (s, 1 H), 5.68 (d, J=8.1 Hz, 1H), 4.20 (dd, J=5.8, 5.8 Hz, 1H), 3.96 (d, J=2.9 Hz, 1H), 3.92 (d, J=3.0 Hz, 1H), 3.82 (s, 6H), 3.47 (dd, J=5.9, 9.7 Hz, 1H), 3.38 (d, I =5.7, 9.6 Hz, 1H).

5'-O-DMT-3'-azido-3'-deoxyarabinouridine (compound 5, FIG. 1) was prepared as follows: To 13.8 g (26 mmol) of 4 in 500 mL acetone was added 200 mL $H_2O$ and 12.0 g (185 mmol) $NAN_3$. The mixture was refluxed overnight, then concentrated/n vacuo to remove the acetone. The resultant slurry was extracted with 600 mL $CH_2Cl_2$, which was in turn was washed with water (3×250 mL). Concentration of the $CH_2Cl_2$ layer and flash chromatography of the crude product provided 6.0 g (40%) of a pale yellow solid. Mass-spectrometry, FAB$^+$, M+H$^+$, calculated: 572.2145, observed: 572.2147. $^1H$ NMR δ 9.4 (br s, 1H), 8.07 (d, J=8.1 Hz, 1H), 7.4–7.3 (mm), 6.89 (d, J=7.9 Hz, 4H), 6.10 (d, J=5.5 Hz, 1H), 5.46 (d, J=8.1 Hz, 1H). 4.55 (m, 1H), 4.19 (dd, J=7.2, 7.7 Hz, 1H), 3.84 (m, 1H), 3.83 (s, 6H), 3.64 (dd J=2.6, 11.3 Hz, 1H), 3.43 (dd, J=2.6, 11.4 Hz, 1H).

5'-O-DMT-2'-fluoro-3'-azido-2',3'-dideoxyuridine (compound 6, FIG. 1) was prepared as follows: To 6.0 g (10.5 mmol) of 5 in 120 mL anhydrous DMF was added 2.4 mL (18.2 mmol) of diethylaminosulfur trifluoride. The mixture was stirred for 16 h, then poured into 300 mL of cold saturated aqueous $NaHCO_3$. The product was extracted with 500 mL ethyl acetate, which in turn was washed with water (2×500 mL). Concentration of the organic layer and flash chromatography of the crude product provided 2.9 g (48%) of an off-white solid. Mass-spectrometry, FAB$^+$, M$^+$, calculated: 573.2024, observed: 573.2011. $^1H$ NMR δ 8.95 (br s, 1H), 7.91 (d, J=8.1 Hz, 1H), 7.2–7.4 (mm, 11H), 6.88 (d, J=8.6 Hz, 4H), 6.02 (d, J=17.2 Hz, 1H), 5.42 (d, J=8.1 Hz, 1H), 5.27 (dd, J=3.7, 55.0 Hz, 1H), 4.24 (m, 1H), ~4.21 (partially overlapping with signal 4.24 ppm, presumed ddd, J=4, 4, -25 Hz, 1H), 3.82 (s, 6H), 3.71 (d, J=11.4 Hz, 1H), 3.49 (d, J=11.3 Hz, 1H); $^{19}F$ NMR δ −196.7 (dddd, est. J=3, 17, 25, 55 Hz).

5'-O-DMT-2'-fluoro-3'-amino-2',3'-dideoxyuridine (compound 6, FIG. 1) was prepared as follows: To 2.9 g (5.1 mmol) of 6 in 75 mL of 95% ethanol was added 0.5 g of 10% palladium on carbon. The mixture was hydrogenated at 40 psi overnight and then the catalyst removed by filtration. The solvent was removed in vacuo, and the resultant solid purified by flash chromatography to give 1.2 g (43%) of product as a white powder. Mass-spectrometry, FAB$^+$, M+H$^+$, calculated: 548.2197, observed: 548.2206. $^1H$ NMR δ 8.04 (d, J=8.0 Hz, 1H), 7.9 (br m, 1H), 7.2–7.4 (mm), 6.85 (d, J=8.4 Hz, 4H), 6.00 (d, J=16.2 Hz, 1H), 5.32 (d, J=8.7 Hz, 1H), 4.83 (dd, J=3.9, 52.2 Hz, 1H), 3.88 (br d, J=11 Hz, 1H), 3.8 (s, 6H), 3.8–3.7 (mm, 2H), 3.52 (dd, J=2.6, 11.1 Hz, 1H); $^{19}F$ NMR δ −200.1 (ddd, J=16.4, 27.5, 52.1 Hz).

EXAMPLE 2

$N^4$-benzoyl-2'-fluoro-3'-(4-methoxytrityl)amino-2',3 '-dideoxyuridine 5'-(2-cyanoethyl N,N-(diisopropyl) phosphoramidite Oligomers of the invention were also synthesized from phosphoramidite monomer, as illustrated by compound 2u of Scheme 2. Uridine 3 was mesylated and then selectively benzoylated with accompanying formation of the 2,2'-anhydrocycle by treatment with sodium benzoate according to literature procedure.[11] These reactions resulted in compound 7 with 69–77% overall yields. By another literature method,[12] 2,3'-anhydroarabinonueleoside 7 was transformed into 2',3'-anhydrolyxoufidine 8 in two steps. This involved treatment of 7 with hydrochloric acid to form 3 '-mesyl-5 '-benzoylarabinouridine, which upon treatment with ammonium hydroxide closed to form the lyxo-2',3'-epoxide 8 in 63–77% overall yields. Then, also according to published procedure,[13] 2',3'-anhydrolyxonucleoside 8 was heated with ammonium azide. Contrary to literature suggestion, this reaction was not completely stereoselective, but produced a chromatographically unresolvable mixture of the desired 5'-benzoyl-3'-azidoarabinonucleoside 9 and it's 2'-azido-2'-deoxyregioisomer 9i in approximately a 2.5:1 ratio. Crude arabinonucleoside 9 was fluorinated with DAST to give 2'-fluoro-3'-azidonucleoside 10, then catalytically hydrogenated to give 2'-fluoro-3'-aminonucleoside 11, which was separable from its regioisomer by silica gel chromatography. Protection of the 3'-amine with a monomethoxytrityl (MMT) group, followed by 5'-debenzoylation produced intermediate 13, with 5'-phosphitylation producing the desired phosphoramidite building block 2u in a 22% overall yield from anhydronucleoside 8. More particularly, the steps were carried out as follows:

3'-O-Methanesulfonyl-5'-O-benzoyl-2,2'-anhydroarabinouridine (compound 7, FIG. 2) was prepared in two steps from 3 (FIG. 2) according to the procedure of Codington et al.[11] in 69–77% overall yields.

5'-O-benzoyl-2',3'-anhydrolyxouridine (compound 8, FIG. 2) was prepared in two steps from 7 according to the procedure of Codington et al.[12] in 63–77% overall yields.

3'-azido-5'-O-benzoyl-3'-deoxyarabinouridine (compound 9, FIG. 2) was prepared from 8 and anhydrous $NH_4N_3$,[20] according to the procedure of Reichman et al.,[13] but without successful recrystallization. Mass yields were 98% or greater, but NMR suggested 25–35% of the regioisomer, 2'-azido-5'-O-benzoyl-2'-deoxyxylouridine, 9i, which coeluted with the desired product by silica gel TLC. $^1$H NMR, Major component, 9: δ 10.8 (br s, 1H), 8.11 (d, J=7.5 Hz, 2H), 7.68 (d, J=8.1 Hz, 1H), 7.62 (d, J=7.3 Hz, 1H), 7.5 (m, 2H), 6.19 (d, J=3.6 Hz, 1H), 5.40, (d, J=8.0 Hz, 1H), 4.84 (m, 1H), 4.73 (d, J=5.7 Hz, 1H), 4.63 (br d, J=4.2 Hz, 1H), 4.2 (mm, 2H); Minor component, 9i: δ 10.6 (br s, 1H), 8.11 (d, J=7.5 Hz, 2H), 7.81 (d, J=8.1 Hz, 1H), 7.64 (d, J=7.5 Hz, 1H), 7.5 (m, 2H), 5.85 (s, 1H), 5.47, (d, J=8.1 Hz, 1H), 4.86 (m, 1H), 4.76 (d, J=5.4 Hz, 1H), 4.62 (br d, J=4.0 Hz, 1H), 4.3–4.2 (mm, 2H).

2'-fluoro-3'-azido-5'-O-benzoyl-2',3'-dideoxyuridine (compound 10, FIG. 2) was prepared as follows: To 5.0 g (13.4 mmol) of crude 9 (containing 25% 9i) in 30 mL anhydrous $CH_2Cl_2$ was added 8.8 mL (66.6 mmol) of diethylaminosulfur trifluoride. After stirring for 48 h, the mixture was diluted with 100 mL $CH_2Cl_2$ and poured into 200 mL saturated aqueous $NaHCO_3$. When evolution of gas ceased, the $CH_2Cl_2$ layer was washed with 100 mL fresh $NaHCO_3$ solution and then with water (2×100 mL). Concentration of the $CH_2Cl_2$ layer in vacuo and flash chromatography gave 3.5 g (70%) of product containing 20% of the largely chromatographically unresolvable isomeric impurity, 10i. $^1$H NMR, Major component, 10: δ 8.7 (br s, 1H), 8.07 (d, J=7.4 Hz, 2H), 7.62 (d, J=7.5 Hz, 1H), 7.49 (dd, J=7.6, 7.6 Hz, 2H), 7.39 (d, J=8.1 Hz, 1H), 5.70 (d, J=21.1 Hz, 1H), 5.65 (d, J=8.2 Hz, 1H), 5.48 (dd, J=4.7, 52.9 Hz, 1H), 4.7–4.4 (unresolved), 4.32 (dd, J=4.7, 9.5 Hz, 1H), 4.27 (dd, J=4.7, 9.5 Hz, 1H); Minor component, 10i: 5 8.7 (br s, 1H), 8.03 (d, J=7.2 Hz, 2H), 7.64 (d, J=7.6 Hz, 1H), 7.51 (dd, J=7.4, 7.7 Hz, 2H), 7.33 (d, J=8.2 Hz, 1H), 5.99 (d, J=6.4 Hz, 1H), 5.67 (d, J=9 Hz, 1H), 5.40 (ddd, J=2.8, 5.0, 53.4 Hz, 1H), 4.8–4.4 (unresolved), 4.10 (mm, 2H).

2'-fluoro-3'-amino-5'-O-benzoyl-2',3'-dideoxyuridine (compound 11, FIG. 2) was prepared as follows: To 3.5 g (9.3 mmol) crude 10 (20% 10i) in 200 mL 95% ethanol was added 600 mg of 10% palladium on carbon. The suspension was hydrogenated at 40 psi overnight and then the catalyst removed by filtration. The solvent was removed in vacuo, giving 2.93 g (90%) of a light yellow solid consisting of two compounds which were resolvable by TLC. Flash chromatography provided 1.96 g (60% yield) of the desired product as a pure white solid. Mass-spectrometry, FAB+, M+H$^+$, calculated: 350.1152, observed: 350.1152. $^1$H NMR δ 8.14 (br s, 1H), 8.06 (d, J=7.1 Hz, 1H), 7.64 (dd, J=7.4, 7.4 Hz, 1H), 7.57 (d, J=8.2 Hz, 1H), 7.50 (dd 7.7, 7.8 Hz, 1H), 5.86 (d, J=18.5 Hz, 1H), 5.51 (d, J=8.2 Hz, 1H) 5.00 (dd, J=4.3, 52.4 Hz, 1H), 4.81 (dd J=2.2, 12.8 Hz, 1H), 4.73 (dd, J=3.5, 12.7 Hz, 1H), 4.14 (ddd, J=2, 3, 10.2 Hz, 1H), 3.57 (ddd, J=4, 10.5, 26.6 Hz, 1H); $^{19}$F NMR δ –198.3 (ddd, J=18.5, 26.4, 52.2 Hz).

2'-fluoro-3'-(4-methoxytrityl)amino-2',3'-dideoxyuridine (compound 12, FIG. 2) was prepared as follows: To 1.0 g (2.9 mmol) of 11 in 50 mL anhydrous pyridine was added 1.0 g (3.2 mmol) 4-methoxytrityl chloride. The mixture was stirred overnight, 5 mL saturated aqueous $NaHCO_3$ was added, and the mixture concentrated in vacuo to an oil. The oil was dissolved in 125 mL ethyl acetate, which was washed with water (3×100 mL) and reconcentrated in vacuo to 2.05 g of foam.

The foam was dissolved in a mixture of 40 mL methanol, 40 mL dioxane, and 10 mL water. NaOH (1 g, 25 mmol) was added and the mixture stirred overnight. The solution was concentrated in vacuo to a syrup, which was dissolved in 100 mL ethyl acetate and washed with water (3×100mL). Concentration in vacuo of the organic layer gave 1.11 g of a foam, which upon flash chromatography gave 1.05 g (76%) of a white solid. Mass-spectrometry, FAB$^+$, M+H$^+$, calculated: 518.2091, observed: 518.2076. $^1$H NMR δ 8.64 (br d J=4.2 Hz, 1H), 8.14 (br s, 1H), 7.57 (mm, 5H), 7.48 (d J=8.7 Hz, 1H), 7.3 (mm, 8H), 6.83 (d J=8.8 Hz, 2H), 5.67 (d, J=17.7 Hz, 1H), 5.62 (d, J=8.1 Hz, 1H), 4.23 (m, 2H), 4.03 (br d, J=10.2 Hz, 1H), 3.80 (s, 3H), 3.31 (dddd, J=3.6, 10.3, 10.9, 25.8 Hz, 1H), 2.80 (dd, J=3.6, 50.9 Hz, 1H), 2.51 (dd, J=3.0, 11.2 Hz, 1H); $^{19}$F NMR δ –192.5 (dddd, J=2.9, 17.7, 26.1, 50.9 Hz).

N$^4$-benzoyl-2'-fluoro-3'-(4-methoxytrityl)amino-2',3'-dideoxyuridine 5'-(2-cyanoethyl N,N-diisopropyl) phosphoramidite (compound 2u, FIG. 2) was prepared as follows: To 700 mg (1.35 mmol) of 12 in 20 mL anhydrous $CH_2Cl_2$ was added 200 mg (1.17 mmol) of diisopropylammonium tetrazolide and 0.5 mL (1.57 mmol) of 2-cyanoethyl N,N,N',N'-tetraisopropylphosphorodiamidite. After stirring the mixture for 3 h, the solvent was removed in vacuo and the residue purified on a Chromatotron, using 4 mm plates and eluting with 0–3% methanol, 0.5% triethylamine in $CH_2Cl_2$. The product was concentrated in vacuo to an oil, which was dissolved in 10 mL $CH_2Cl_2$ and precipitated by slow addition into 100 mL of rapidly stirred hexane. After decanting the supernatant, the product was vacuum desiccated over $P_2O_5$, giving 680 mg (70%) of white powder. Mass-spectrometry, FAB$^+$, M+H$^+$, calculated: 718.3170, observed: 718.3194. $^{19}$F NMR δ –190.9 (ddd, J=21.7, 21.8, 51.3 Hz); $^{31}$P NMR δ 150.5, 149.5.

EXAMPLE 3

N$^4$-benzoyl-2'-fluoro-3'-(4-methoxytrityl)amino-2',3'-dideoxycytidine 5'-(2-cyanoethyl N,N-diisopropyl) phosphoramidite Crude intermediate 10 was used for preparation of the appropriately protected cytidine phosphoramidite 2c (Scheme 3, FIG. 3). The uracil base of 10 was converted to cytosine by adaptation of the method of Reese et al.[14] Subsequent 4-N benzoylation and reduction of the 3'-azido to an amino group gave compound 13, which was separable from its regioisomer by silica gel chromatography. Protection of the 3'-amine with an MMT group, followed by selective 5'-O-debenzoylation produced intermediate 15. Subsequent 5'-phosphitylation lead to desired phosphoramidite 2c in a 10% overall yield based on anhydronucleoside 8. More particularly, the steps were carried out as follows:

$N^4$,5'-O-dibenzoyl-2'-fluoro-3'-amino-2',3'-dideoxycytidine (compound 13, FIG. 3) was prepared as follows: To 6.9 g (18.4 mmol) of crude 10 (containing 35% 10i) in 50 mL anhydrous $CH_3CN$ was added an ice-cold solution of 11.7 g (169 mmol) 1,2,4-triazole and 3.35 mL (36.1 mmol) $POCl_3$ in 90 mL anhydrous $CH_3CN$. The mixture was cooled in an ice bath and anhydrous triethylamine (23 mL, 165 mmol) was added, then the reaction allowed to warm to room temperature with stirring. After 90 min, 15 mL (108 mmol) triethylamine and 4 mL water were added and the mixture stirred for 10 min. The solvent was removed in vacuo, then 250 mL ethyl acetate was added, and the solution was TLC indicated a fluorescent intermediate with the same mobility as the starting material.

The mixture was concentrated in vacuo to 6.7 g of a foam. Dioxane (100 mL) and 20 mL concentrated aqueous ammonia were added, and after 3 h, the mixture was concentrated in vacuo to a yellow gel. The gel was dissolved in 100 mL ethyl acetate and washed with water (3×200 mL). Concentration in vacuo and vacuum desiccation over $P_2O_5$ yielded 5.4 g of a solid which gave only one spot by silica gel TLC. Only two significant signals were observed by $^{19}F$ NMR, Major component: δ −192.8 (ddd, J=22.8, 22.8, 53.1 Hz); Minor component: δ −200.7 (ddd, J=13.6, 19.9, 53.4 Hz).

Anhydrous pyridine (100 mL) was added and the solution cooled to 4° C. Benzoyl chloride (11.7 mL 100 mmol) was added with stirring and the mixture allowed to warm to room temperature. After 2 h, 5 mL water was added and the solvent removed in vacuo, giving a brown oil, which was dissolved in 200 mL ethyl acetate, washed with water (3×200 mL), and then reconcentrated in vacuo to an oily foam.

Ethanol (150 mL) and 2 g of 10% palladium on activated carbon were added and the mixture was hydrogenated at 40 psi $H_2$ overnight. TLC indicated formation of two new slower, closely-migrating compounds.

The catalyst was removed by filtration, and the filtrate concentrated in vacuo to an oily yellow foam. Silica gel flash chromatography (500 mL silica, eluted with 0–3% $CH_3OH$ in $CH_2Cl_2$) provided 1.85 g of semi-pure product, which was dissolved in 10 mL $CH_2Cl_2$. A solid quickly precipitated, which was collected by filtration and washed with fresh $CH_2Cl_2$. Vacuum desiccation yielded 1.5 g of product 13 (11% yield from 9 and 9i) as free white crystals. Mass-spectrometry, $FAB^+$, $M+H^+$, calculated: 453.1574, observed: 453.1574. $^1H$ NMR δ 8.21 (d, J=7.5 Hz, 1H), 8.08–8.13 (mm, 3H), 7.94 (d, J=7.4 Hz, 2H), 7.46–7.7 (mm, 8H), 6.04 (d, J=16.9 Hz, 1H), 5.08 (dd, J=3.6, 51.5 Hz, 1H), 4.85 (dd, J=3.3, 12.8 Hz, 1H), 4.80 (dr, J=2.1, 12.8 Hz, 1H), 4.26 (m, 1H), 3.48 (dm, J=27 Hz, 1H); $^{19}F$ N/VIR δ −200.1 (m).

$N^4$,5'-O-dibenzoyl-2'-fluoro-3'-(4-methoxytrityl) amino-2',3'-dideoxycytidine (compound 14, FIG. 3) was prepared as follows: To 0.9 g (2.0 mmol) of 13 in 25 mL anhydrous pyridine was added 0.86 g (2.8 mmol) 4-methoxytrityl chloride, and the mixture stirred overnight. The reaction was quenched with 0.5 mL $H_2O$ and concentrated in vacuo. $CH_2Cl_2$ (50 mL) was added and washed with 50 mL saturated aqueous $NaHCO_3$ and with water (2×50 mL). The solvent was removed in vacuo, replaced with 10 mL $CH_2Cl_2$, and pipetted into 80 mL rapidly stirred 1/1 hexane/ether. After further stirring for 2 h, the product was collected by filtration and dried under vacuum, giving 1.3 g (88% yield) of product as a white powder. Mass-spectrometry, $FAB^+$, $M+H^+$, calculated: 725.2775, observed: 725.2761. $^1H$ NMR δ 8.59 (br s, 1H), 8.07 (br d, J=5.7 Hz, 1H), 7.89 (br d, J=7 Hz, 2H), 7.83 (dd, J=1.3, 6.7 Hz, 2H), 7.68 (dd, J=7.4, 7.4 Hz, 2H), 7.5–7.6 (m, 8H), 7.43 (dd, J=2.1, 6.9 Hz, 2H), 7.1–7.3 (mm, 7H), 6.71 (d, J=8.9 Hz, 2H), 5.80 (d, J=15.4 Hz, 1H), 5.03 (dd,J=2.0, 13.0 Hz, 1H), 4.98 (dd, J=2.3;, 13.1 Hz, 1H), 4.41 (br d, J=10.5 Hz, 1H), 3.63 (s, 3H), 3.36 (dddd, J=3.1, 11.1, 11.1, 25.7 Hz, 1H), 2.84 (dd, J=3.1, 49.9 Hz, 1H), 2.52 (dd, J=2.7, 11.5 Hz, 1H); $^{19}F$ NMR δ −196.3 (m).

$N^4$-benzoyl-2'-fluoro-3'-(4-methoxytrityl) amino-2',3'-dideoxycytidine (compound 15, FIG. 3) was prepared as follows: To 1.3 g (1.75 mmol) of 14 in 20 mL of 65/30/5 pyridine/methanol/water, cooled in an ice bath, was added 10 mL of cold 2M NaOH in 65/30/5 pyridine/methanol/water. The mixture was stirred cold for 20 min, then neutralized with pyridinium-$H^+$ form Bio-Rad AG® 50W-X8 cation exchange resin. After 5 min, the resin was removed by filtration and washed with methanol. The combined filtrate and wash were concentrated in vacuo to an oil, which was dissolved in 100 mL ethyl acetate. The mixture was washed with 100 mL saturated aqueous $NaHCO_3$ and with water (2×100mL). After concentration in vacuo to a foam, the product was dissolved in 10 mL $CH_2Cl_2$ and pipetted into 75 mL rapidly stirred hexane/ether, 2/1. The product was collected by filtration and dried under vacuum, giving 1.13 g (102% yield) of product as a white powder. Mass-spectrometry, $FAB^+$, $M+Cs^+$, calculated: 753.1489, observed: 753.1499. $^1H$ NMR δ 8.30 (br d, J=6.8 Hz, 1H), 7.89 (br d, J=6.7 Hz, 2H), 7.64 (dd, J=7.4, 7.4 Hz, 1H), 7.44–7.56 (mm, 9H), 7.22–7.32 (mm, 9H), 6.82 (d, J=8.8 Hz, 2H), 5.80 (d, J=15.7 Hz, 1H), 4.26 (mm, 2H), 4.13 (d, J=10.2 Hz, 1H), 3.81 (s, 3H), 3.26 (dddd, J=3.4, 10.7, 10.8, 26.5 Hz, 1H), 2.93 (dd, J=3.3, 50.5 Hz, 1H), 2.50 (dd, J=2.8, 11.0 Hz, 1H); $^{19}F$ NMR δ −195.3 (m).

$N^4$-benzoyl-2'-fluoro-3'-(4-methoxytrityl)amino-2',3'-dideoxycytidine 5'-(2-cyanoethyl N,N-diisopropyl) phosphoramidite (compound 2c, FIG. 3) was prepared as follows: To 970 mg (1.56 mmol) of 15 in 25 mL anhydrous $CH_2Cl_2$ was added 200 mg (1.17 mmol) of diisopropylammonium tetrazolide and 1.0 mL (3.15 mmol) of 2-cyanoethyl N,N,N',N'-tetraisopropylphosphorodiamidite. After stirring the mixture for 3 h, the solvent was removed in vacuo and the residue purified on a Chromatotron, using 4 mm plates and eluting with 0–1.5% methanol in 0.5% triethylamine in $CH_2Cl_2$. The product was concentrated in vacuo to a foam, which was dissolved in 10 mL $CH_2Cl_2$, and precipitated by slow addition to 40 mL of rapidly stirred hexane. After decanting the supernatant, the product was vacuum desiccated over $P_2O_5$, giving 880 mg (69%) of white powder. Mass-spectrometry, $FAB^+$, $M+Cs^+$, calculated: 953.2568, observed: 953.2531. $^{19}F$ NMR δ −193.6 (m); $^{31}P$ NMR δ 150.4, 149.4.

EXAMPLE 4

$N^4$-benzoyl-2'-fluoro-3'-(4-methoxytrityl)amino-2',3'-dideoxycytidine 5'-succinyl-loaded CPG Intermediate 15 was 5'-succinylated and loaded upon CPG solid support by standard procedures.15,16 More, particularly, $N^4$-benzoyl-2'-fluoro-3'-(4-methoxytrityl) amino-2',3'-dideoxycytidine 5'-succinyl-loaded CPG was prepared as follows: To 100 mg (0.16 mmol) of 15 in 2 mL anhydrous $CH_2Cl_2$ was added 55 mg (0.55 mmol) of succinic anhydride and 65 mg (0.53 mmol) of dimethylaminopyridine. The mixture was stirred for 2 h, the evaporated in vacuo to an oil. The oil was dissolved in 20 mL $CH_2Cl_2$, washed with 20 mL of saturated aqueous $NaHCO_3$ and with water (2×20mL), and then reconcentrated in vacuo to a foam. To the foam was added 1 mL 0.4M diisopropylethylamine in DMSO/N-methylpyrrolidine, 1/1, and 0.7 mL 0.2M 1-hydroxybenzotriazole, 0.2M 2-(1H-benzotriazol-1-yl)-1,1,3,3-tetramethyluronium hexafluorophosphate in DMSO/N-methylpyrrolidine, 1/1. After 3 min, the mixture was drawn into a 10 mL syringe containing 1.2 g of long-chain alkylamino-CPG. An additional 5 mL DMSO wash was also drawn into the syringe. The CPG-nucleoside mixture was mixed for 1.5 h, then the CPG washed with 5 volumes of anhydrous acetonitrile. Unreacted CPG amino groups were acetylated by standard ABI capping solutions for 2 min. The CPG was again washed with 5 volumes of acetonitrile and 5 volumes of $CH_2Cl_2$. Nucleoside loading was determined to be approximately 5 μmole/g by standard trityl assay.

EXAMPLE 5

Solid Phase Synthesis of Oligo-2'-fluoronucleotide N3'→P5' Phosphoramidates

Oligo-2'-fluoronucleotide N3'→P5' phosphoramidates were synthesized on solid phase supports using either 5'-DMT-2'-fluoro-3'-aminonucleoside monomers (Scheme 1) or phosphoramidite monomers (of Schemes 2 and 3).

Dimer $dU^f_{np}T$ was prepared using monomer of Scheme 1 via carbon tetrachloride-driven oxidative phosphorylation of $dU^f_n$ by a 5'-H-phosphonate of the anchored dT. Product was analyzed and isolated by RP HPLC in 70% yield and the structure was confirmed by mass spectrometry and by acid catalyzed hydrolysis, which gave 2'-fluoro-3'-amino-2'-deoxyuridine and 5'-thymidylic acid. The same synthetic strategy was also used to introduce one or two 2'-fluoro-3'-aminonucleosides into longer oligonucleotide phosphoramidate chains. Compounds 20 and 21, Table 1, containing one or two 2'-fluoronucleosides in the middle of the chain were prepared and isolated by IE HPLC. Coupling yields of the 2'-fluoronucleoside 1 did not exceed 70–75% (in contrast to 94–96% for the 2'-deoxynucleosides), as judged by stepwise measurement of released DMT-cation and by IE HPLC analysis.

Figure 6:
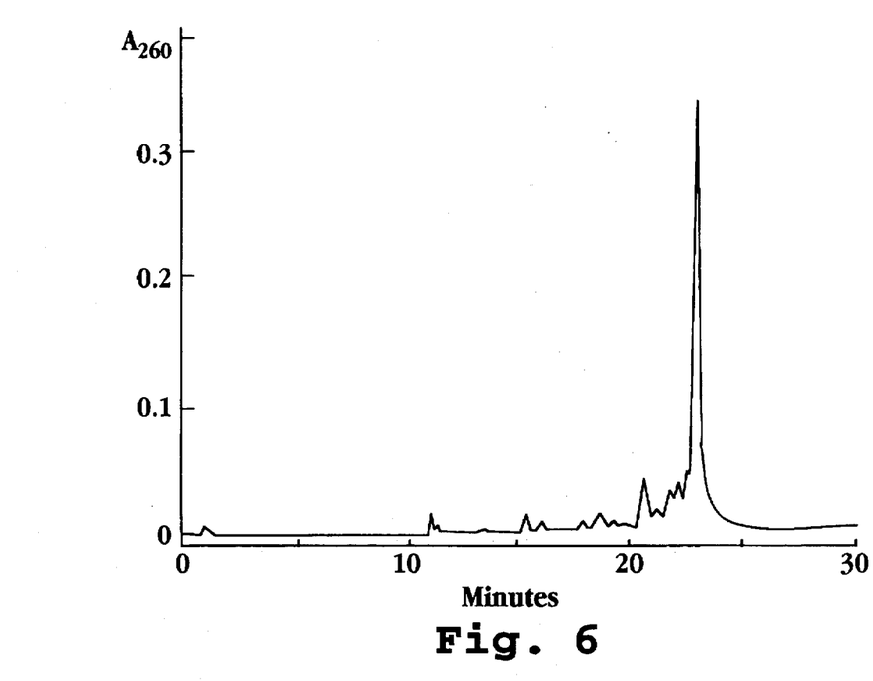
FIG. 6 is an ion exchange HPLC chromatogram of the crude reaction mixture from synthesis of an oligo-2'-fluoronucleoside N3'→P5' phosphoramidate of Example 5.

Compounds 22–25 (Table 1) were synthesized by way of phosphoramidite monomers. The average coupling efficiency as determined by released MMT-cation assay was ~94% with single coupling per cycle and ~96% with double application of Step 2 per synthetic cycle. A representative IE HPLC profile of a crude oligomer synthesis is shown in FIG. 6.

EXAMPLE 6

Thermal Stability of Duplexes of RNA or DNA and Oligo-2'-fluoronucleotide Phosphoramidates The ability of the oligo-2'-fluoronucleoside phosphoramidates to hybridize with complementary DNA and RNA was evaluated. Melting temperatures were determined for duplexes formed under close to physiological salt concentrations and the results are summarized in Table 1. Substitution of one 2'-deoxynucleoside by one 2'-fluoronucleoside in a phosphoramidate decamer lead to an increase in $T_m$ by ~2° C. for either DNA or RNA hybrids (expt. 2 and 3, Table 1). Accordingly, replacement of two 2'-deoxynucleosides with 2'-fluoronucleosides in the same phosphoramidate decamer led to an increase in duplex's $T_m$ of 3.5°–6.4° C. In contrast, others have reported that substitution with two central 2'-fluoronucleosides destabilizes the duplexes of phosphodiester oligomers.[17]

Substitution of all 2'-fluoronucleosides for 2'-deoxynucleosides in the decamer phosphoramidate resulted in significant enhancement of duplex thermal stability: $T_m$ values were increased by 16°–25° C. (compare expt. 2 and 5, Table 1). The presented data show that further increases in the proportion of N-sugar ring pucker in the N3'→P5' phosphoramidates as well as additional negative polarization of 3'-amino groups (by 2'-fluorine) substantially stabilized oligonucleotide duplexes. It is noteworthy that $T_m$'s of the duplexes formed by 2'-fluoroamidates were 38°–44° C. higher than those of isosequential phosphodiester compounds, with 4°–5° C. per modification increase in melting temperatures (compare expt 1, 5, and 6, Table 1). Addition of magnesium cation to the melting buffer stabilized duplexes formed by phosphoramidates with DNA to a greater extent than those formed with RNA, suggesting a probable different secondary structure and solvation of the complexes being formed.

The same trend in duplex thermal stability was observed for mixed-base 11-mer 25 (Table 1), which formed more stable hybrids with complementary DNA and RNA than did the analogous oligo-2'-deoxynucleoside phosphoramidate 24 (compare expt. 7 and 8, Table 1).

TABLE 1

Oligonucleotides and $T_m$ values of their duplexes.

| | | $T_m$, °C.[b] | |
|---|---|---|---|
| Expt | Oligonucleotide[a] | DNA[c] | RNA[c] |
| 1 | UUUUUUUUUT, 18 | 16.7; 24.6 | 17.9; 20.3 |
| 2 | $U_{np}U_{np}U_{np}U_{np}U_{np}U_{np}U_{np}U_{np}U_{np}T$, 19 | 18.5; 38.2 | 38.1; 47.2 |
| 3 | $U_{np}U_{np}U_{np}U_{np}U^f_{np}U_{np}U_{np}U_{np}U_{np}T$, 20 | 20.0; 41.0 | 40,1; 49.3 |
| 4 | $U_{np}U_{np}U_{np}U^f_{np}U^f_{np}U_{np}U_{np}U_{np}U_{np}T$, 21 | 23.4; 44.6 | 44.5; 52.7 |
| 5 | $_pU^f_{np}U^f_{np}U^f_{np}U^f_{np}U^f_{np}U^f_{np}U^f_{np}U^f_{np}U^f_{np}T$, 22 | 34.6; 63.0 | 55.2; 64.6 |
| 6 | $_pU^f_{np}U^f_{np}U^f_{np}U^f_{np}U^f_{np}U^f_{np}U^f_{np}U^f_{np}U^f_{np}U^f_n$, 23 | 39.5; 63.2 | 56.4; 64.0 |
| 7 | $C_{np}U_{np}U_{np}C_{np}U_{np}U_{np}C_{np}C_{np}U_{np}A$, 24 | 44.2; — | 66.0; — |
| 8 | $C^f_{np}U^f_{np}U^f_{np}C^f_{np}U^f_{np}U^f_{np}C^f_{np}C^f_{np}U^f_{np}U^f_{np}A$, 25 | 56.9; — | 81.6; — |

[a]All 2'-deoxy compounds; np, f, p, and n represent 3'-NHP(O)(O⁻)O-5' internucleoside link, 2'-fluorine, 5'-phosphate, and 3'-amine, respectively;
[b]$T_m$ was determined with 3 μM of oligonucleotides; first values were determined in 10 mM sodium phosphate, 150 mM sodium chloride, pH 7.04; second values were determined in same buffer containing an additional 10 mM magnesium chloride; dashes are for not determined $T_m$s.
[c]complementary target; poly(dA) or poly(rA) for experiments 1–6, d(ATAAGGAAGAAGC) or r(AUAAGGAAGAAGC) for experiments 7, 8.

EXAMPLE 7

Hydrolytic Stability of Oligo-2'-fluoronucleotide Phosphoramidates

Stability of the oligo-2'-fluoro- in comparison with the oligo-2'-deoxynucleotide N3'→P5' phosphoramidates toward enzymatic hydrolysis was evaluated. Phosphoramidates 19 and 22 (Table 1) were treated with snake venom phosphodiesterase and alkaline phosphatase, and analyzed at successive time points by IE HPLC. Under the conditions used, oligo-2'-deoxyphosphoramidate 19 and oligo-2'-fluorophosphoramidate 22 were hydrolyzed progressively and at similar rates, with calculated half-lives of the full-length strands equal to 4.9 and 5.4 h, respectively. In comparison, decathymidilic acid with natural phosphodiester linkages was completely digested to thymidine within 10 min under the same conditions.

The stability of the phosphoramidates toward acid-catalyzed hydrolysis was studied as follows. Oligonucleotides 19 and 22 were incubated at room temperature in 10% acetic acid, pH 2.2 or in 20 mM sodium acetate buffers, pH 4.7 and 5.3. The hydrolysis reactions were monitored by IE HPLC and the data are summarized in Table 2. The observed half-lives of full-length oligonucleotide 19 at pH 2.2, 4.7, and 5.3 were 21.5 min, 12.3 h, and 68 h, respectively. The oligo-2'-fluorophosphoramidate 22 was noticeably more stable under these conditions, with respective half-lives of this full-length oligomer of 61 min, 66 h, and 309 h. These results demonstrate a markedly reduced 3'-nitrogen basicity due to electron-withdrawing 2'-fluorine, with consequently greater acid stability of oligo-2'-fluorophosphoramidates relative to the parent oligo-2'-deoxyphosphoramidates.

TABLE 2

Acid Stability of the Oligonucleotide N3'→P5' Phosphoramidates

| | | $T_{1/2}$, h pH | |
|---|---|---|---|
| Expt Oligonucleotide | 2.2 | 4.7 | 5.3 |
| 1  $U_{np}U_{np}U_{np}U_{np}U_{np}U_{np}U_{np}U_{np}U_{np}T$, 19 | 0.34 | 12.3 | 68 |
| 2  $_pU^f_{np}U^f_{np}U^f_{np}U^f_{np}U^f_{np}U^f_{np}U^f_{np}U^f_{np}U^f_{np}T$, 22 | 1.0 | 66 | 309 |

Cited References 1. (a) Helene, C.; Toulme, J. J. *Biochem. Biophys. Acta* 1990, 1049, 99–125.
   (b) Uhlman, E.; Peyman, A. *Chem. Rev.* 1990, 90, 544–584
2. (a) Bielinska, A.; Shivdasami, R. A.; Zhang, L.; Nabel, G. J. *Science* 1990, 250, 997–101.
   (b) Wyatt, J. R.; Vickers, T. A.; Roberson, J. L.; Buckheit, R. W. Jr.; Klimkait, T.; DeBeats, E.; Davis, P. W.; Rayner, B.; Imbach, J. L.; Ecker, D. J. *Proc. Natl. Acad. Sci., USA* 1994, 91, 1356–1360.
3. DeMesmacker, A.; Altman, K. H.; Waldner, A.; Wendebom, S. *Curr Opinion Struct. Biol.* 1995, 5, 343–355.
4. (a) Gryaznov, S.M.; Chen, L K. *J. Am. Chem. Soc.* 1994, 116, 3143–3144.
   (b) Gryaznov, S. M.; Lloyd, D. H.; Chen, J. K.; Schultz, R. G.; DeDionisio, L. A.; Ratmeyer, L.; Wilson, W. D. *Proc. Natl. Acad. Sci., USA* 1995, 92, 5798–02.
   (c) Chen, J. K.; Schultz, R. G.; Lloyd, D. H.; Gryaznov, S. M. *Nucleic Acids Res.* 95, 23, 2661–2668.
5. Ding, D.; Gryaznov, S. M.; Lloyd, D. H.; Chandrasekaran, S.; Yao, S.; Ratmeyer, L.; Li Pan, Y.; Wilson, W. D. *Nucleic Acids Res.* 1996, 24, in press.
6. Gryaznov, S. M.; Letsinger, R. L. *Nucleic Acids Res.* 1992, 20, 3403–3409.
7. (a) Kawasaki, A. M.; Casper, M. D.; Freier, S. M. Lesnik, E. A.; Zounes, M. C.; Cummins, L. L.; Gonzalez, C.; Cook, P. D. *J. Med. Chem.* 1993, 36, 831–841.
   (b) Monia, B. P.; Lesnik, E. A.; Gonzalez, C.; Lima, W. F.; McGee, D.; Guinosso, C. J.; Kawasaki, A. M.; Cook, P. D.; Freier, S .M. *J. Biol. Chem.* 1993, 268, 514–14522.
8. Pieken, W. A.; Olsen, D. B.; Benseler, F.; Aurup, K.; H.; Eckstein, F. *Science* 91, 253, 314–317.
9. (a) Ikehara, M. *Heterocycles* 1984, 21, 75–90.
   (b) Guschlbauer, W.; Jankowski, K. *Nucleic Acids Res.* 1980, 8, 1421–1433.
10. Webb, T. R.; Mitsuya, H.; Broder, S. *J. Med. Chem.* 1988, 31, 1475–1479.
11. Codington, J. F.; Fecher, R.; Fox, J. J. *J. Am. Chem. Soc.* 1960, 82, 2794–03.
12. Codington, J. F.; Fecher, R.; Fox, J. J. *J. Organic Chem.* 1962, 27, 163–167.
13. Reichman, U.; Hollenberg, D. H.; Chu, C. K.; Watanabe, K. A.; Fox, J. J. *J. Organic Chem.* 1976, 41, 2042–2043.
14. Divakar, K. J.; Reese, C. B. *J. Chem. Soc., Perkin. Trans.* 1 1982, 1171–76.
15. Atkinson, T.; Smith, M. In *Oligonucleotide Synthesis. A Practical Approach*, Gait, M. J. Ed., IRL Press, 1984, 35–81.
16. Knorr, R.; Trzeciak, A.; Bannwarth, W.; Gillessen, D. *Tetrahedron Lat.* 1989, 30, 1927–1930.
17. Williams, D. M.; Beuseler, F.; Eckstein, F. *Biochemistry* 1991, 30, 4001–09.
18. Caruthers, M. H. *Accounts Chem. Res.* 1991, 24, 278–284.
19. Gryaznov, S. M.; Letsinger, R. L. *Nucleic Acids Res.* 1993, 21, 1403–1408.
20. Obenland, C. O.; Mangold, D. J.; Marino, M. P. *Inorg. Synth.* 1966, 8, 53–56.

---

We claim:

1. A polynucleotide comprising an oligo-2'-fluoronucleoside N3'→P5' phosphoramidate segment defined by the formula:

wherein B is a purine or pyrimidine, n is an integer greater than 1, and $R^4$ is hydrogen or a phosphate protecting group.

2. The polynucleotide of claim 1, wherein $R^4$ is hydrogen or a phosphate protecting group selected from the group consisting of methyl, β-cyanoethyl, or 4-nitrophenylethyl.

3. The polynucleotide of claim 1, wherein n is an integer between 2 and 30.

4. The polynucleotide of claim 3, wherein n is an integer between 2 and 20.

5. The polynucleotide of claim 1, wherein B is a pyrimidine.

6. The polynucleotide of claim 1 in a triplex comprising said polynucleotide and a target double-stranded DNA.

7. The polynucleotide of claim 1, wherein the oligo-2'-fluoronucleoside N3'→P5' phosphoramidate segment is defined by the formula:

wherein $R^1$ is hydroxyl or a 5'-hydroxyl protecting group.

8. The polynucleotide of claim 7, wherein $R^1$ is hydroxyl or a trityl group.

9. The polynucleotide of claim 7, wherein $R^4$ is hydrogen or a phosphate protecting group selected from the group consisting of methyl, β-cyanoethyl, or 4-nitrophenylethyl.

10. The polynucleotide of claim 7, wherein n is an integer between 2 and 30.

11. The polynucleotide of claim 10, wherein n is an integer between 2 and 20.

12. The polynucleotide of claim 7, wherein B is a pyrimidine.

13. The polynucleotide of claim 7 in a triplex comprising said polynucleotide and a target double-stranded DNA.

14. The polynucleotide of claim 7, wherein $R^1$ is hydroxyl, $R^4$ is H, and n is an integer greater than 8.

15. The polynucleotide of claim 14, wherein n is an integer between 8 and 20.

16. The polynucleotide of claim 15, hybridized to double-stranded DNA to form a triplex.

* * * * *